US005972601A

United States Patent [19]
Newman

[11] Patent Number: 5,972,601
[45] Date of Patent: *Oct. 26, 1999

[54] METHODS AND KITS FOR DETERMINING THE PEN POLYMORPHISM OF HUMAN PLATELET MEMBRANE GLYCOPROTEIN IIIA

[75] Inventor: Peter J. Newman, Bayside, Wis.

[73] Assignee: Blood Center Research Foundation, Inc., Milwaukee, Wis.

[*] Notice: This patent is subject to a terminal disclaimer.

[21] Appl. No.: 08/484,201

[22] Filed: Jun. 7, 1995

Related U.S. Application Data

[63] Continuation-in-part of application No. 07/721,321, Jul. 1, 1991, abandoned.

[51] Int. Cl.$^6$ ..................................................... C12Q 1/68
[52] U.S. Cl. ............................ 435/6; 530/324; 536/24.31
[58] Field of Search ...................... 435/6, 91.2; 530/324; 536/24.3, 24.31

[56] References Cited

U.S. PATENT DOCUMENTS

| 5,091,302 | 2/1992 | Newman et al. ............................ 435/6 |
| 5,177,188 | 1/1993 | Ginsberg et al. ......................... 530/324 |

FOREIGN PATENT DOCUMENTS

| 0-117-934 | 9/1984 | European Pat. Off. . |
| WO 90/03983 | 4/1990 | WIPO . |
| WO 90/06953 | 6/1990 | WIPO . |
| WO 90/12593 | 11/1990 | WIPO . |
| WO9012593 | 11/1990 | WIPO . |
| WO 91/08306 | 6/1991 | WIPO . |
| WO9301315 | 1/1993 | WIPO . |

OTHER PUBLICATIONS

Wang, R. et al. 1992 J. Clin. Invest 90 : 2038–2043.
Fitzgerald, L. 1987 J.Biol.Chem vol. 262 (9): 3936–3939.
Zimrin, A.B. 1990 J.Biol. Chem vol. 265 (2): 8590–8595.
Fitzgerald et al., "Glycoprotein Sequence of Endothelial Glycoprotein IIIa Derived from cDNA Clone," *J. Biol. Chem.* 262: 3936–3939 (Mar. 25, 1987).
Furihata et al., "On the Association of the Platlet–specific Alloantigen, Pen$^a$, with Glycoprotein IIIa: Evidence for Heterogeneity of Glycoprotein IIIa," *J. Clin. Invest.* 80: 1624–1630 (Dec. 1987).
Inostroza et al., "Frequency of platelet–specific antigens Pl$^{A1}$, Yuk$^a$,Yuk$^b$, and Br$^a$ in South American (Mapuches) Indians," *Transfusion* 28: 586–587 (1988).
Newman et al., "Enzymatic Amplification of Platelet–specific Messenger RNA Using the Polymerase Chain Reaction," *J. Clin. Invest.* 82: 739–743 (Aug. 1988).
Newman et al., "The Human Platelet Alloantigens, Pl$^{A1}$ and Pl$^{A2}$, Are Associated with a Leucine$^{33}$/Proline$^{ee}$ Amino Acid Polymorphism in membrane Glycoprotein IIIa . . . " *J. Clin. Invest.* 83: 1778–1781 (May 1989).
Shibata et al., "Yuk$^a$, A New Platelet Antigen Involved in Two Cases of Neonatal Alloimmune Thrombocytopenia," *Vox Sang.* 50: 177–180 (1986).
Shibata et al., "A New Platelet Antigen System, Yuk$^a$/Yuk$^b$," *Vox Sang.* 51: 334–336 (1986).
Simon et al., "Posttransfusion Purpura Associated With Alloantibody Specific for the Platelet Antigen, Pen$^a$, " *Am. J. Hematol.* 29: 38–40 (1988).
Wang et al., "Sequence Variation of Human Platelet Membrane Glycoprotein IIIa Associated with the Yuk$^a$/Yuk$^b$ Alloantigen System," *Proc. Japan Acad.* 67:102–106 (Sep. 1991).
Wang et al., "An Amino Acid Polymorphism within the RGD Binding Domain of Platelet Membrane Glycoprotein IIIa is Responsible for the Formation of the Pen$^a$/Pen$^b$ . . . " *J. Clin. Invest.* 90: 2038–2043 (Nov. 1992).
Zimrin et al., "The Genomic Organization of Platelet Glycoprotein IIIa," *J. Biol. Chem.* 265: 8590–8595 (May 25, 1990).
Derwent Abstracts for Japanese patent document No. JP2300664 and U.S. patent No. 5,288,610.

*Primary Examiner*—James Ketter
*Assistant Examiner*—Irem Yucel

[57] ABSTRACT

Isolated polynucleotide molecules and peptides encoded by these molecules can be used in the analysis of alloantigen phenotypes, as well as in diagnostic and therapeutic applications, relating to human platelet Pen polymorphism. By analyzing genomic DNA or amplified genomic DNA, or amplified cDNA derived from platelet mRNA, it is possible to type glycoprotein GPIIIa with regard to the Pen polymorphism, for example, in the context of diagnosing and treating clinical syndromes associated with GPIIIa-related immune responses.

27 Claims, No Drawings

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO:1:

ACAAGCTAGC CCATTGCCAA ACAGG                                        25

(2) INFORMATION FOR SEQ ID NO:2:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO:2:

AAAGGGACCA GGGCTTTCTG GTTTG                                        25

(2) INFORMATION FOR SEQ ID NO:3:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO:3:

CACCTGGTCA GTTAGCGTCA GCACG                                        25

(2) INFORMATION FOR SEQ ID NO:4:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO:4:

CATGTGTGCC TGGTGCTCTG ATG                                                                    23

(2) INFORMATION FOR SEQ ID NO:5:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:5:

AATACGACTC ACTATAG                                                                           17

(2) INFORMATION FOR SEQ ID NO:6:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:6:

ATTTAGGTGA CACTATAG                                                                          18

(2) INFORMATION FOR SEQ ID NO:7:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:7:

CCAGGTCACT CAAGTCAG                                                                          18

(2) INFORMATION FOR SEQ ID NO:8:

(i) SEQUENCE CHARACTERISTICS:
       (A) LENGTH: 13 base pairs
       (B) TYPE: nucleic acid
       (C) STRANDEDNESS: single
       (D) TOPOLOGY: linear (xi) SEQUENCE DESCRIPTION: SEQ ID NO:8:

AGATGCGAAA GCT                                                                               13

(2) INFORMATION FOR SEQ ID NO:9:

(i) SEQUENCE CHARACTERISTICS:
       (A) LENGTH: 13 base pairs
       (B) TYPE: nucleic acid
       (C) STRANDEDNESS: single
       (D) TOPOLOGY: linear (xi) SEQUENCE DESCRIPTION: SEQ ID NO:9:

AGATGCAAAA GCT                                                                               13

METHODS AND KITS FOR DETERMINING THE PEN POLYMORPHISM OF HUMAN PLATELET MEMBRANE GLYCOPROTEIN IIIA

This application is a continuation of U.S. patent application Ser. No. 07/721,321, filed Jul. 1, 1991, abandoned.

The invention of this Application was made in work funded by grants from the U.S. National Institutes of Health. The United States Government has certain rights in the invention.

BACKGROUND OF THE INVENTION

The present invention relates to isolated polynucleotide molecules useful for analyzing alloantigen phenotypes, to peptides encoded by these molecules, and to the diagnostic and therapeutic uses thereof relating to the "Pen" human platelet polymorphism. Among such uses is a method for typing platelet membrane glycoproteins which entails an analysis either of genomic DNA or of amplified cDNA produced from platelet mRNA.

Blood obtained from different individuals has been found to have different antigenic and immune properties, to the extent that antibodies in the blood of one person may react with antigens on red blood cells or platelets in the blood of another individual. These antigens are often found on membrane glycoproteins present on the surface of the cells. These membrane glycoprotein antigens can induce the production of antibodies against them when they are introduced as foreign proteins in transfused blood or in fetal blood. Human platelets and red blood cells contain dozens of identifiable membrane glycoprotein constituents, only some of which have been well characterized.

Membrane glycoproteins which induce antibody production in the same species are called "alloantigens." Alloantigens have been characterized for both red blood cells and platelets. Recognized classes of red blood cell and platelet alloantigens have been described, over the past 30 years, based on observations of antibody reactions occurring when patients have been exposed to blood from other individuals.

One system of alloantigens, consisting of the platelet $Pen^a$ and $Pen^b$ alloantigens, are carried by the human platelet membrane glycoprotein IIb-IIIa (GPIIb-IIIa) complex, which mediates platelet aggregation by providing functional receptors for fibrinogen on platelet surfaces. See Friedman & Aster, *Blood* 65:1412–1415 (1985). Further investigation has revealed that the Pen alloantigen system is located on GPIIIa. See Shibata & Mori, *Proc. Japan Acad.* 63:36–38 (1987).

GPIIIa is known to bear at least one other clinically important, alloantigenic determinant, $Pl^A$, which is responsible for eliciting an immune response in two well-described clinical syndromes, post-transfusion purpura (PTP) and neonatal alloimmune thrombocytopenia (NATP). See Kunicki & Newman in CURRENT STUDIES IN HEMATOLOGY AND BLOOD TRANSFUSION 18–32 (1986); Aster in ADVANCES IN IMMUNOLOGY AND BONE MARROW TRANSPLANTATION 103–118 (1984). While polymorphisms such as $Pl^A$ on GPIIIa and Bak located on GPIIb are most often implicated in PTP and NATP in Caucasian and black populations, the Pen alloantigen system is the most frequent cause of these disorders in oriental individuals. See Shibata & Mori, *Proc. Japan Acad.* 63:36–38 (1987); Furihata et al., *J. Clin. Invest.* 80:1624–1630 (1987).

There are two serologically defined allelic forms of the Pen alloantigen which are designated "$Pen^a$" and "$Pen^b$."

The location of the Pen antigen system, like that of $Pl^A$, has been shown to be associated with the GPIIIa molecule. See Shibata & Mori, loc. cite and Furihata et al. loc. cite. The gene frequencies for these two alleles in the Japanese population have been calculated to be 99.8% for $Pen^a$ and 0.2% for $Pen^b$. See Shibata et al., *Vox Sang.* 51:334 (1986); Simon et al., *Amer. J. Hematol.* 29:38–40 (1988).

The immunological characteristics of blood group alloantigens have often been attributed to the extensive glycosylation of these proteins. Differences in glycosylation may be due to either generic variation among glycosylation enzymes, as in the ABO alloantigen system, or to amino acid-sequence polymorphisms among the alloantigens themselves, or to a combination of these factors as in the MN system. See Eisen et al., IMMUNOLOGY (2d ed. 1980). In particular, differences in specific sialic acid structures have been determined to contribute to the expression of actual allogenic epitopes. See Sadler et al., *J. Biol. Chem.* 254(6):2112–2119 (1979); Take et al., *British J. Haematol.* 76:395–400 (1990). The basis for the variations responsible for the relevant epitopes has not yet been reported for either the Pena or $Pen^b$ forms of the 100 kilodalton (kd) GPIIIa molecule.

SUMMARY OF THE INVENTION

It is therefore an object of the present invention to provide polynucleotide molecules that can be used in analyzing Pen alloantigen.

It is also an object of the present invention to provide for the typing of human platelets to determine Pen phenotype, based on information obtained through the analysis of nucleic acids, including genomic DNA and cDNA derived from platelets, respectively.

It is yet another object of the present invention to provide ready means for determining platelet Pen alloantigen phenotype.

It is still a further object of the present invention to provide polypeptide molecules for use in generating antibodies that distinguish between the different forms of GPIIIa which constitute the Pen polymorphism.

Another object of the present invention is to provide methods for diagnosing and treating clinical syndromes related to a GPIIIa-related immune response.

In achieving these objects, there has been provided, in accordance with one aspect of the present invention, an oligonucleotide probe molecule that hybridizes to a portion of the GPIIIa gene, which portion includes a nucleotide corresponding to nucleotide 526 of GPIIIa cDNA, where the molecule hybridizes under stringent conditions to the portion in question when nucleotide 526 is guanylate, for one type of allele-specific probe, or adenylate for another type. In a preferred embodiment, the oligonucleotide probe of the present invention is between about ten and thirty bases in length.

In accordance with another aspect of the present invention, a kit for typing platelet Pen alloantigens has been provided comprising
  (a) means for amplifying DNA that comprises at least a portion of a GPIIIa gene or GPIIIa cDNA, wherein the portion includes a nucleotide corresponding to nucleotide 526 of GPIIIa cDNA, and
  (b) a receptacle containing a solution of a labeled oligonucleotide probe that distinguishes an allele of a platelet Pen alloantigen from another Pen allele.

In accordance with a further aspect of the present invention, a kit for typing platelet Pen alloantigens has been provided comprising a receptacle containing a solution of an antibody that discriminately binds a Pen$^a$ allele or a Pen$^b$ allele of GPIIIa, where the antibody (i) recognizes a polypeptide molecule encoded by a nucleotide sequence encoding at least amino acid 143 of GPIIIa and (ii) binds either the Pen$^a$ allele or the Pen$^b$ allele of GPIIIa.

There has also been provided, in accordance with another aspect of the present invention, a method of typing glycoprotein IIIa, comprising the steps of (A) synthesizing cDNA from human platelet mRNA of an individual; (B) amplifying the cDNA to produce amplified cDNA; and then (C) analyzing the amplified cDNA to determine Pen alloantigen phenotype for that individual. In one preferred embodiment, the method further comprises synthesizing cDNA from human platelet mRNA of a second individual, repeating aforementioned steps (B) and (C) on the cDNA of second individual, and thereafter discriminating between the first and second individuals based on the Pen alloantigen phenotype.

In accordance with yet another aspect of the present invention, a method of typing platelet Pen membrane glycoproteins has been provided that comprises the steps of (A) obtaining genomic DNA from an individual and (B) analyzing the genomic DNA to determine a platelet Pen alloantigen phenotype. In one preferred embodiment, the method further comprises synthesizing cDNA from human platelet mRNA of a second individual, repeating aforementioned steps (B) and (C) on the cDNA of second individual, and thereafter discriminating between the first and second individuals based on the Pen alloantigen phenotype. In another preferred embodiment, step (B) comprises (i) digesting the genomic DNA with a restriction endonuclease to produce DNA fragments; thereafter (ii) hybridizing the DNA fragments with a labeled, allele-specific oligonucleotide probe that distinguishes a nucleotide sequence of an allele of a platelet Pen alloantigen from other alleles; and then (iii) analyzing the probe that has hybridized to the DNA fragments in order to determine the Pen alloantigen phenotype. In yet another preferred embodiment, a method is provided wherein step (B) comprises the steps of (i) hybridizing genomic DNA with a pair of oligonucleotide probes to produce a construct, wherein a first probe of the pair is labeled with a first label and a second probe of the pair is labeled with a second label, such that the first label is distinguishable from the second label, and the pair of probes hybridize adjacently to each other at a nucleotide of the genomic DNA that distinguishes a Pen allele from another Pen allele; thereafter (ii) reacting the construct with a ligase in a reaction medium; and then (iii) analyzing the reaction medium to detect the presence of a ligation product comprising the first probe and the second probe.

In accordance with still another aspect of the present invention, there has been provided a method of typing platelets to identify a Pen alloantigen phenotype that comprises the steps of (A) obtaining genomic DNA from an individual, (B) amplifying the genomic DNA to produce amplified genomic DNA and (C) analyzing the amplified genomic DNA to determine a platelet Pen alloantigen phenotype. In a preferred embodiment, step a further comprises obtaining genomic DNA from a second individual and then repeating steps (B) and (C) on the genomic DNA of the second individual and thereafter discriminating between the first and second individuals based on the alloantigen phenotype. In another preferred embodiment, step (C) comprises of (i) hybridizing the amplified genomic DNA with a labeled, allele-specific oligonucleotide probe that distinguishes a nucleotide sequence of a Pen allele from that of another Pen allele; and then (ii) analyzing the probe that has hybridized to the amplified genomic DNA to determine said alloantigen phenotype. In another preferred embodiment, step (C) comprises (i) hybridizing the amplified genomic DNA with a pair of oligonucleotide probes to form a construct, wherein a first probe of the pair of probes is labeled with a first label and the other probe is labeled with a second label, such that the first label is distinguishable from the second label, and the probes hybridize adjacently to each other at a nucleotide that distinguishes a Pen$^a$ allele from a Pen$^b$ allele; thereafter (ii) reacting said construct with a ligase in a reaction medium; and then (iii) analyzing said reaction medium to detect the presence of a ligation product comprising the first probe and the said second probe.

A polypeptide molecule is further provided, in accordance with another aspect of the present invention, that comprises an amino-acid sequence that corresponds to a tetramer fragment of GPIIIa, wherein the fragment comprises amino acid 143 of GPIIIa and wherein the molecule is not GPIIIa itself. Preferably, the polypeptide molecule is between four and fifty amino-acid residues in length. In addition, it is preferred that the polypeptide molecule is itself immunogenic or is attached to a immunogenicity-imparting carrier, forming another molecule of the present invention.

According to another aspect of the present invention, an antibody is provided that distinguishes the Pen$^a$ form of GPIIIa antigen from the Pen$^b$ form, where the antibody recognizes a polypeptide sequence that comprises at least amino acid 143 of GPIIIa. The antibody can be a monoclonal antibody produced by a method comprising the steps of (A) immunizing a mammal with an antigenic molecule comprising a polypeptide as described above, then (B) removing lymphocytes from the mammal, (C) fusing the lymphocytes with mammalian myeloma cells to form hybridoma cells, (D) culturing the hybridoma cells and thereafter (E) selecting, isolating and cloning hybridoma cells secreting monoclonal antibodies that distinguish between the Pen$^a$ and Pen$^b$ forms of GPIIIa.

A method is also provided, pursuant to another aspect of the present invention, for treating post-transfusion purpura or neonatal alloimmune thrombocytopenia, comprising the step of administering to an individual a formulation comprised of a peptide in a pharmacologically effective concentration and a physiologically-compatible carrier therefor, where the individual (i) suffers from post-transfusion purpura or is the mother of a fetus at risk for developing NATP and (ii) has anti-Pen$^a$ or anti-Pen$^b$ antibodies, said peptide binding an antibody selected from the group consisting of an anti-Pen$^a$ antibody and an anti-Pen$^b$ antibody.

In accordance with yet another aspect of the present invention, an isolated DNA molecule has been provided that comprises a nucleotide sequence corresponding to a portion of the GPIIIa gene that includes a nucleotide corresponding to nucleotide 526 of GPIIIa cDNA, wherein the molecule is not coincident with the GPIIIa gene.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

It has been discovered that a single nucleotide of the GPIIIa gene is responsible for the Pen polymorphism. In light of this discovery, manipulation of mRNA derived from platelets can be effected to provide for the analysis of alloantigen phenotypes, for the generation of peptides encoded by such nucleic acid and for the use of such peptides in diagnosis and therapy relating to a human platelet Pen polymorphism. Nucleic-acid molecules utilized in these contexts may be amplified, as described below, and generally include RNA, genomic DNA and cDNA derived from RNA.

Although the generation of cDNA from platelet mRNA was previously thought to be unfeasible, a new approach has been discovered for examining platelet mRNA from single individuals. As described in U.S. Pat. No. 5,091,302, the contents of which are hereby incorporated by reference, it has been found that mRNA can be obtained from platelets in quantities sufficient for isolation, cDNA generation, and amplification. By generating and amplifying cDNA produced from mRNA of a number of individuals of known platelet allotypes, nucleotide sequence variations that may exist in genes that express alloantigen determinants can be ascertained.

To obtain amplified cDNA from platelet mRNA, mRNA derived from platelets via conventional methods, see, e.g., MANIATIS, ET AL., MOLECULAR CLONING: A LABORATORY MANUAL 187–210 (Cold Spring Harbour Laboratory, 1982), can be converted to cDNA and then enzymatically amplified to produce microgram quantities of platelet-specific cDNA. This amplification is preferably accomplished via the "polymerase chain reaction" (PCR) method disclosed by U.S. Pat. Nos. 4,683,195 and 4,800,159, the respective contents of which are hereby incorporated by reference.

More specifically, in the process of generating and amplifying cDNA encoded by the isolated platelet mRNA, oligonucleotide primer pairs can be constructed that allow enzymatic amplification of a cDNA segment obtained from an mRNA molecule that encodes an amino-acid sequence defining the polymorphism. The corresponding, isolated cDNAs can then be analyzed to determine the molecular basis of observed phenotypic differences. The ability to compare directly the nucleotide and corresponding amino-acid sequences of genes encoding alleles of alloantigens is made possible by (1) the discovery that cDNA can be generated and amplified successfully from platelet mRNAs and (2) the determination of a nucleotide sequence of a glycoprotein which is thought to be polymorphic.

The molecular description of polymorphisms associated with platelet alloantigens can be provided by analyzing amplified cDNA, generated from platelet mRNA, according to one of the following methods: allele-specific oligonucleotide probing (ASOP) and ligase-mediated gene detection (LMGD). Additional methods of analysis would also be useful in this context, such as fluorescence resonance energy transfer (FRET) as disclosed by Wolf et al., *Proc. Nat. Acad. Sci. USA* 85:8790–8794 (1988), the contents of which are hereby incorporated by reference.

In ASOP analysis according to conventional methods, oligonucleotide probes are synthesized that will hybridize, under appropriate annealing conditions, exclusively to a particular amplified cDNA segment that contains a nucleotide sequence that distinguishes one allele from other alleles of a platelet membrane glycoprotein. Such a probe would be discernably labeled so that when it hybridizes to the allele-distinguishing cDNA segment, it can be detected and the specific allele thus identified.

For example, an oligonucleotide probe can be synthesized, in accordance with the present invention, that will hybridize to a cDNA segment, derived from GPIIIa mRNA, that contains the base guanine at polymorphic nucleotide 526. (nucleotide=guanylate). Alternatively, an oligonucleotide probe of the present invention will hybridize when the cDNA segment contains the base adenine at nucleotide 526. (nucleotide=adenylate). These allele-specific probes can be appropriately labeled and added to the generated cDNA segments under annealing conditions, such that one of the allele-specific probes hybridizes and can be detected, thereby identifying the specific $Pen^a$ or $Pen^b$ allele. In accordance with conventional procedures, the design of an oligonucleotide probe according to the present invention preferably involves adjusting probe length to accommodate hybridization conditions (temperature, ionic strength, exposure time) while assuring allele-specificity. A length of ten to thirty nucleotides is typical.

In the course of the third method of analysis, LMGD, as disclosed by Landegren, et al., *Science* 241:1077–1080 (1988), the contents of which are hereby incorporated by reference, a pair of oligonucleotide probes are synthesized that will hybridize adjacently to each other, i.e., to a cDNA segment under appropriate annealing conditions, at the specific nucleotide that distinguishes one allele from other alleles of a platelet membrane glycoprotein. Each of the pair of specific probes is labeled in a different manner, and, when both probes hybridize to the allele-distinguishing cDNA segment, the probes can be ligated together by the addition of a ligase.

When the ligated probes are separated and isolated from the cDNA segments, both types of labeling can be observed together on a Northern blot when analyzed by conventional procedures, confirming the presence of the allele-specific nucleotide sequence. Where the above-described pair of differently labeled probes bind to a nucleotide sequence containing a distinguishing nucleotide of a different allele, the probe pair is not ligatable and, after the probes are isolated from the cDNA segments, each type of labeling is observed to be separate from the other label type.

An exemplary LMGD analysis, according to the present invention, entails the use of a pair of oligonucleotide probes, wherein one probe is radioactively $^{32}P$-labeled and the other probe is biotin-labeled. Under appropriate conditions, the pair of probes adjacently hybridizes to a cDNA segment at a nucleotide corresponding to nucleotide 526 of GPIIIa. The biotin-labeled probe hybridizes to nucleotides 506–526 of GPIIIa, wherein nucleotide 526 contains an adenine, which distinguishes the $Pen^b$ allele. The $^{32}P$-labeled probe hybridizes nucleotides 527–537 of GPIIIa and, therefore will hybridize adjacently to the biotin-labeled probe. These probes are then added under annealing conditions such that they hybridize adjacently to each other, spanning nucleotides 506–537 of GPIIIa. The biotin-labeled probe is detected by the binding of the compound strepavidin after hybridization and the $p^{32}$-labeled probe is detected by autoradiography, according to conventional procedures.

When the $Pen^b$ allele sequence is present in the amplified cDNA, then the addition of a ligase will result in the biotin-labeled probe being covalently bound to the $^{32}p$-labeled probe. The ligation is possible, because the ends of the probes that are adjacent to each other (hybridized to nucleotides (526 and 527) are both hybridized to the cDNA. In the case where these two probes hybridize to the $Pen^a$ allelic form of the cDNA sequence, the biotin-labeled probe end at nucleotide 526 is not hybridized appropriately, preventing the ligation step from occurring. When this pair of probes binds completely to the $Pen^b$ allele sequence, therefore, the probes are ligated and when the probes are separated from the Pen$^b$ sequence and exposed so as to be detected, both the biotin/strepavidin and the $^{32}$p labeling are present together. When the Pen$^a$ allele sequence is hybridized, on the other hand, the probes cannot be ligated, and the biotin/strepavidin- and $^{32}$p-labeling are observed separately. In this manner, the Pen$^b$ and Pen$^a$ alleles sequences and corresponding phenotype can be distinguished.

Alternatively, ASOP and LMGD or other suitable methods of analysis, such as FRET, can be used with genomic or amplified-genomic DNA to distinguish platelet membrane glycoprotein Pen$^b$ from Pen$^a$, starting with any nucleated cell sample, obtained from an individual, from which DNA can be isolated in sufficient quantities for analysis. Amplified genomic DNA would be amplified from isolated genomic DNA in the same manner as described above for cDNA. Once a tissue sample, such as cells scraped from the inside of an individual's cheek, has been obtained, genomic DNA isolated by conventional procedures can be analyzed directly per se or amplified prior to analysis.

The foregoing description of the three types of analysis would apply to the use of genomic DNA or amplified-genomic DNA, with the term "cDNA" being replaced with "genomic or amplified genomic DNA." One difference in the analysis of genomic DNA or amplified genomic DNA is that the GPIIIa sequence used for designing a suitable oligonucleotide probe might have to include any intronic sequences, which would not be present in the cDNA of GPIIIa, that were near or adjacent to the nucleotide that determines the Pen phenotype.

In general, the presence of intronic sequences near the phenotype-determining nucleotide can be ascertained by sequence analysis of genomic DNA accomplished via Maxam-Gilbert or another conventional technique. Sequence information on the region of genomic DNA encompassing an exon that encodes the polymorphism can be used to design appropriate oligonucleotides, such that a genomic DNA-based PCR could be performed. The resulting amplified products can then be assessed for alloantigen phenotype, in accordance with the present invention, by means of any of the above-described diagnostic methods. More generally, the primers used for PCR amplification should be positioned, relative to the exon which contains the polymorphic nucleotide, so that the amplified region encompasses that nucleotide, which corresponds to base 526 of the GPIIIa cDNA. In a particularly preferred embodiment of the present invention, an anti-sense primer (5'ACAAGCTAGCCCATTGCCAAACAGG-3'), SEQ ID NO:1, and a sense primer (5'-AAAGGGACCAGGGCTTTCTGGTTTG-3'), SEQ ID NO:2, are employed in conventional PCR methods for amplifying genomic DNA.

The ability to perform DNA-typing analysis for determination of Pen phenotypes, pursuant to the present invention, has a number of useful clinical applications, including but not limited to those involving determination of the Pen alloantigen phenotype of an individual, and the diagnosis and treatment of a pathological immune response (or potential response) involving foreign alloantigens or antibodies. In accordance with the present invention, alloantigen phenotyping can be effected by the generation of amplified genomic DNA from, for example, fetal-derived cells from samples of amniotic fluid or amplified cDNA from platelet mRNA, permitting diagnosis of individuals for the purpose of treating or preventing pathological immune responses.

Once the nucleotide-sequence variations specific for each allelic form of the alloantigens of a given class are determined, other conventional methods can be employed, through the use of genomic DNA or platelet RNA, to perform the same type of diagnosis on other individuals. These methods would include, but not are limited to, allele-specific nucleotide probing and ligase-mediated gene detection, as previously described.

Diagnostic kits can also be used, in accordance with the present invention, for the determination and diagnosis of alloantigen phenotypes via the procedures described herein. Such a kit can include, inter alia, antibodies or antibody fragments to an antigenic determinant expressed by either of the above-described Pen$^a$- and Pen$^b$-encoding sequences, which antibodies would react with the blood sample of an individual so as to indicate whether that individual has a Pen$^a$ or Pen$^b$ phenotype. Alternatively, all the reagents required for the detection of nucleotide(s) that distinguish the Pen alloantigens, by means described herein, can be provided in a single kit that uses isolated genomic DNA or platelet mRNA from an individual. Containing a labeled probe that distinguishes, for example, nucleotide 526 of GPIIIa, such a kit can be utilized for Pen alloantigen phenotyping.

A further beneficial use of the nucleotide sequences that distinguish the Pen$^a$ allele from the Pen$^b$ allele is to obtain or synthesize the respective expression product, in the form of a polypeptide, encoded by these nucleotide sequences. These polypeptides can be used to generate antibodies for diagnostic and therapeutic uses, for example, with regard to pathological conditions such as PTP or NATP.

A polypeptide within the present invention which can be used for the purpose of generating such antibodies preferably comprises an amino-acid sequence that corresponds to (i.e., is coincident with or functionally equivalent to) a four-residue (tetramer) fragment of the GPIIIa molecule that includes amino acid 143. When the latter amino acid is arginine, the polypeptide can be used, as described above, to produce antibodies that specifically bind the Pen$^a$ form of GPIIIa; when it is glutamine, antibodies can be obtained that particularly recognize the Pen$^b$ form. The class of polypeptides thus defined, in accordance with the present invention, is not intended to include the GPIIIa molecule itself, but does encompass fragments of the molecule as well as synthetic polypeptides meeting the aforementioned definition.

Although the length of a polypeptide within this class is not critical, the requirement for immunogenicity may require that the polypeptide be attached to a immunogenicity-imparting carrier, e.g., a particulate carrier like a liposome or a soluble macromolecule (protein or polysaccharide) with a molecular weight in the range of about 10,000 to 1,000,000, or be administered with an adjuvant, such as complete Freund's adjuvant. For artificial polypeptides, as distinguished from GPIIIa fragments, maximum length is determined largely by the limits of techniques available for peptide synthesis, say, about fifty amino acids. Thus, a synthetic polypeptide of the present invention is preferably between four and about fifty amino acids in length.

In this context, the term "antibody" encompasses monoclonal and polyclonal antibodies. Such an antibody can belong to any antibody class (IgG, IgM, IgA, etc.). For monoclonal antibody (Mab) production, one generally proceeds by isolating lymphocytes and fusing them with myeloma cells, producing hybridomas. The cloned hybridomas are then screened for production of antibodies the bind preferentially to either the Pen$^a$ form or the Pen$^b$ form of GPIIIa. "Antibody" also encompasses fragments, like Fab and F(ab')$_2$, of anti-Pen$^a$ or anti-Pen$^b$ antibodies, and conjugates of such fragments, and so-called "antigen binding proteins" (single-chain antibodies) which are based on anti-Pen$^a$ or anti-Pen$^b$ antibodies, in accordance, for example, with U.S. Pat. No. 4,704,692, the contents of which are hereby incorporated by reference. Human alloantisera currently used for serological typing are specifically excluded from this definition. Alternatively, Mabs or a fragment thereof within the present invention can be produced using conventional procedures via the expression of isolated DNA which codes for variable regions of such an Mab in host cells like *E. coli*, see, e.g., Ward et al., *Nature*, 341:544–546 (1989), or transfected murine myeloma cells. See Gillies et al., *Biotechnol.* 7:799–804 (1989); Nakatani et al., *Biotechnol.* 7:805–810 (1989).

Diagnostic applications of these antibodies are exemplified, according to the present invention, by the use of a kit containing an anti-Pen$^a$ or an anti-Pen$^b$ antibody which undergoes a reaction with a sample of an individual's blood to determine a Pen$^a$ or Pen$^b$ platelet phenotype. Such a reaction involves the binding of anti-Pen$^a$ antibody to Pen$^a$ antigen or the binding of anti-Pen$^b$ antibody to Pen$^b$ antigen. The observation antibody-antigen complex in a blood sample would indicate a positive result. A kit of this sort could be used to diagnose, or to help prevent, the occurrence of pathological conditions like PTP or NATP.

A polypeptide of the present invention that is recognized specifically by anti-Pen$^a$ or anti-Pen$^b$ antibodies can be used therapeutically. Thus, antibodies raised against such a polypeptide can employed in the generation, via conventional methods, of anti-idiotypic antibodies (that is, antibodies that bind an anti-Pen$^a$ or anti-Pen$^b$ antibody), for example, by the use of hybridomas as described above. See, for example, U.S. Pat. No. 4,699,880, the contents of which are hereby incorporated by reference. Such anti-idiotypic antibodies would bind endogenous or foreign anti-Pen antibodies in the blood of an individual, thereby to treat or prevent pathological conditions associated with an immune response to a "foreign" Pen alloantigen. Alternatively, a polypeptide within the present invention can be administered, with a physiologically-compatible carrier, to achieve the same qualitative effect, namely, the selective reduction or elimination of circulating anti-Pen antibodies from a patient suffering or at risk from an immune response.

The present invention is further described below by reference to the following, illustrative examples. Used in the examples were platelet samples from ten homozygous Pen$^a$ individuals, one homozygous Pen$^b$ individuals, and two individuals who were heterozygous for the Pen allotype. The respective phenotypes of all the test subjects had been identified using well-characterized anti-Pen$^a$ and anti-Pen$^b$ human alloantisera.

EXAMPLE 1

AMPLIFICATION OF cDNA

Platelet RNA from a panel of thirteen normal volunteers, including ten Pen$^{a/a}$, one Pen$^{b/b}$ and two Pen$^{a/b}$ individuals, was prepared according to the procedure developed by Chomczynski and Sacchi, *Anal. Biochem.* 162:156 (1987), except that the final RNA pellet was subjected to one additional phenol/chloroform extraction and ethanol precipitation necessary to achieve reproducible gene amplification of platelet cDNA. Pen$^a$ and Pen$^b$ phenotype was assessed using well-characterized human alloantisera in a standard antigen capture assay, see Furihata et al., *J. Clin. Invest.* 80:1624 (1987); Chomczynski and Sacchi, *Anal. Biochem.* 162:156 (1987). The C-terminal end of the GPIIIa chain message from base 161–698 was selected for sequence analysis and comparison, and a 23-base oligonucleotide primer and a 25-base oligonucleotide primer flanking 490 base pairs of this region were synthesized on a Gene Assembler (Pharmacia Fine Chemicals, Piscataway, N.J.).

The anti-sense primer (5'-CACCTGGTCAGT TAGCTTCAGCAGG-3'), SEQ ID NO:3, from base 698 to 674 was used to prime the synthesis of cDNA from platelet RNA as previously described (Newman et al.,*J. Clin. Invest.* 82:739 (1988); Newman et al., *J. Clin. Invest.* 83:1778 (1989). The second strand was generated by the sense primer (5'-CATGTGTGCCTGGTGCTCTGATG-3'), SEQ ID NO:4, from base 161 to 183 during the first round of PCR. Amplification was carried out in a DNA Thermal Cycler (Perkin-Elmer Cetus, Norwalk, Conn.) proarammed to permit denaturation at 94° C. for 90 seconds, annealing at 50° C. for 90 seconds, and chain extension at 72° C. for three minutes. The reaction was allowed to proceed for 30 cycles followed by a final incubation at 72° C. for seven minutes to allow completion of strand synthesis.

EXAMPLE 2

ANALYSIS OF PCR PRODUCTS

PCR samples were analyzed on 1.8% Seakem GTG agarose gels (FMC BioProducts, Rockland, Me.), and the appropriate bands were excised and recovered by electroelution. The plasmid vector pGEM-5Zf (Promega Biotech, Madison, Wis.) was prepared for ligation by restriction digestion with Eco RV (New England Biolabs, Beverly, Md.) to yield blunt ends, and ligated to purified amplification product, followed by transformation into *E. coli* strain NM522 competent cells (Stratagene Cloning Systems, San Diego, Calif.). Two clones representing each Pen homozygous phenotype were selected for direct sequence analysis of the plasmid DNA by the dideoxy sequencing method using T7 DNA polymerase (USB, Cleveland, Ohio USA). The following oligonucleotides were synthesized and used as sequencing primers:

T7 primer: 5'-AATACGACTCACTATAG-3', SEQ ID NO:5,

SP6 primer: 5'-ATTTAGGTGACACTATAG-3', SEQ ID NO:6,

Primer (332–349): 5'-CCAGGTCACTCAAGTCAG-3', SEQ ID NO:7,.

The results demonstrated that a single nucleotide difference was observed between the Pen$^{a/a}$ and Pen$^{b/b}$ clones at base 526. Analysis of the cDNA derived from Pen$^{a/a}$ individuals revealed that guanine was present at this position, whereas adenine was substituted in this position in the Pen$^{b/b}$ cDNA. This resulted in a substitution of an arginine for an glutamine at amino acid residue 143.

EXAMPLE 3

ALLELE-SPECIFIC HYBRIDIZATION

Amplified cDNA from ten individuals with Pen$^{a/a}$ phenotype, one with Pen$^{b/b}$, and two heterozygous for Pen was subjected to hybridization with thirteen-base allele-specific oligonucleotides (ASO). The sequence of Probe A is (5'-AGATGCGAAAGCT-3'), SEQ ID NO:8,. Probe B (5'-AGATGCAAAAGCT-3'), SEQ ID NO:9, differs only in the middle base, an A instead of a G, and corresponds to a single base difference observed in the region sequenced. The probes (200ng) were end-labeled with digoxigenin-11-dUTP (Boehringer Mannheim, Indianapolis, Ind.) in 25 ml 100 mmol/L potassium cacodylate, 2 mmol/L $CoCl_2$, 0.2 mmol/L DTT, pH 7.2 containing 1 U terminal transferase (Boehringer Mannheim, Indianapolis, Ind.), and the probes were used for hybridization without purification. Amplified DNA was used directly for blotting or, in some cases, appropriate bands were recovered from agarose gels using Gene Clean (Bio 101, LaJolla, Calif.). The samples were eluted in 20 ml water, diluted 1/10,000, and 10 ml was used for reamplification using the same primers and PCR conditions. Amplified or reamplified DNA was denatured in 0.25 N NaOH, 1.5 mol/L NaCl at room temperature for 15 minutes. Each sample was divided between two wells of a Minifold dot blot apparatus (Schleicher and Schuell, Keene, N.H.) and transferred to Magnagraph nylon membrane (MSI, Westboro, Md.) by vacuum suction. The filter was exposed to UV irradiation (Fotodyne, New Berlin, Wis.) for 5 minutes followed by baking at 80° C. for 15 minutes. The membrane was prehybridized in 5× Denhardt's, 5× SSC, 10 mmol/L EDTA, 10 mmol/L $Na_2HPO_4$, pH 7 at 68° C. for one hour, and then cut into two strips which were hybridized to either Probe A or Probe B in 4 ml 10× Denhardt's 5× SSC, 5mmol/L EDTA, 7% SDS, 50 ug/ml Salmon sperm DNA, 20 mmol/l $Na_2HPO_4$, pH 7 at 35° C. overnight. The filters were washed in 2 changes 6× SSC for 30 minutes each at room temperature followed by 2 changes of 3 mol/L tetramethylammonium chloride (Aldrich Chemical, Milwaukee, Wis.), 2 mmol/L EDTA, 1% SDS, 50 mmol/L Tris, pH 8 for 20 minutes each at 35° C. Positive hybridizations using The Genius kit (Boehringer Mannheim, Indianapolis, Ind.) which employs an alkaline phosphatase-conjugated anti-digoxigenin antibody, according to the manufacturer's directions.

The results demonstrated that Probe A was positive with the ten $Pen^{a/a}$ homozygous individuals, Probe B was positive with the one $Pen^{b/b}$ homozygous individual, and both probes were positive with amplified DNA from the two heterozygous individuals analyzed.

What is claimed is:

1. A method of typing glycoprotein GPIIIa, comprising the steps of (A) synthesizing cDNA from human platelet mRNA of a first individual; (B) amplifying said cDNA to produce amplified cDNA; and then (C) analyzing said amplified cDNA to determine Pen alloantigen phenotype for said first individual.

2. A method as claimed in claim 1, further comprising the step of synthesizing cDNA from human platelet mRNA of a second individual, and then repeating steps (B) and (C) on the cDNA of said second individual; and thereafter discriminating between said first and second individuals based on said alloantigen phenotype.

3. A method as claimed in claim 1, wherein step (C) comprises the steps of (i) hybridizing said cDNA fragments with a labeled allele-specific oligonucleotide probe that distinguishes a nucleotide sequence of a Pen allele from another Pen allele; and then (ii) detecting any of said probe that has hybridized to said cDNA fragments to determine said Pen alloantigen phenotype.

4. A method as claimed in claim 3, wherein said Pen allele comprises a sequence that is encoded by at least nucleotide 526 of GPIIIa mRNA and said labeled oligonucleotide probe hybridizes to a nucleotide sequence which comprises or is adjacent to nucleotide 526 of GPIIIa mRNA.

5. A method as claimed in claim 1, wherein step (C) comprises the steps of
 (i) hybridizing said amplified cDNA with a pair of oligonucleotide probes to produce a construct, wherein a first probe of said pair is labeled with a first label and a second probe of said pair is labeled with a second label, such that the first label is distinguishable from the second label, and the probes hybridize adjacently to each other at a nucleotide that distinguishes a first Pen allele from another Pen allele; thereafter
 (ii) reacting said construct with a ligase in a reaction medium; and then
 (iii) analyzing said reaction medium to detect the presence of a ligation product comprising said first probe and said second probe.

6. A method as claimed in claim 5, wherein said Pen allele comprises a sequence that is encoded by at least nucleotide 526 of GPIIIa mRNA and one of said labeled oligonucleotide probes hybridizes to a nucleotide sequence which comprises nucleotide 526 of GPIIIa mRNA.

7. A method of typing platelet Pen membrane glycoproteins comprising the steps of (A) obtaining genomic DNA from a first individual and (B) analyzing said genomic DNA to determine a platelet Pen alloantigen phenotype.

8. A method as claimed in claim 7, further comprising the step of obtaining genomic DNA from a second individual, and then repeating step (B) on the genomic DNA of said second individual; and thereafter discriminating between said first and second individuals based on said Pen alloantigen phenotype.

9. A method as claimed in claim 7, wherein step (B) comprises the steps of
 (i) digesting said genomic DNA with a restriction endonuclease to produce DNA fragments; thereafter
 (ii) hybridizing said DNA fragments with a labeled allele-specific oligonucleotide probe that distinguishes a nucleotide sequence of an allele of a platelet Pen alloantigen from other alleles; and then
 (iii) analyzing said probe that has hybridized to said DNA fragments to determine said Pen alloantigen phenotype.

10. A method as claimed in claim 9, wherein said Pen allele comprises a sequence that is encoded by at least nucleotide 526 of GPIIIa mRNA and said labeled oligonucleotide probe hybridizes to a nucleotide sequence which comprises nucleotide 526 of GPIIIa mRNA.

11. A method as claimed in claim 7, wherein step (B) comprises the steps of
 (i) hybridizing said genomic DNA with a pair of oligonucleotide probes to produce a construct, wherein a first probe of said pair is labeled with a first label and a second probe of said pair is labeled with a second label, such that the first label is distinguishable from the second label, and the pair of probes hybridize adjacently to each other at a nucleotide of said genomic DNA that distinguishes a Pen allele from another Pen allele; thereafter
 (ii) reacting said construct with a ligase in a reaction medium; and then
 (iii) analyzing said reaction medium to detect the presence of a ligation product comprising said first probe and said second probe.

12. A method as claimed in claim 11, wherein said Pen allele comprises a sequence that is encoded by at least nucleotide 526 of GPIIIa mRNA and said labeled oligonucleotide probe hybridizes to a nucleotide sequence which comprises or is adjacent to nucleotide 526 of GPIIIa mRNA.

13. A method of typing platelets to identify a Pen alloantigen phenotype, comprising the steps of (A) obtaining genomic DNA from an first individual, (B) amplifying said genomic DNA to produce amplified genomic DNA and (C) analyzing said amplified genomic DNA to determine a platelet Pen alloantigen phenotype.

14. A method as claimed in claim 13, further comprising the step of obtaining genomic DNA from a second individual, and then repeating steps (B) and (C) on the genomic DNA of said second individual; and thereafter discriminating between said first and second individuals based on said alloantigen phenotype.

15. A method as claimed in claim 13, wherein step (C) comprises the steps of
 (i) hybridizing said amplified genomic DNA with a labeled allele-specific oligonucleotide probe that distinguishes a nucleotide sequence of a Pen allele from that of another Pen allele; and then
 (ii) analyzing said probe that has hybridized to said amplified genomic DNA to determine said alloantigen phenotype.

16. A method as claimed in claim 15, wherein said Pen allele comprises a sequence that is encoded by at least nucleotide 526 of GPIIIa mRNA and said labeled oligonucleotide probe hybridizes to a nucleotide sequence which comprises or is adjacent to nucleotide 526 of GPIIIa mRNA.

17. A method as claimed in claim 13, wherein step (C) comprises the steps of
 (i) hybridizing said amplified genomic DNA with a pair of oligonucleotide probes to form a construct, wherein a first probe of said pair is labeled with a first label and a second probe of said pair is labeled with a second label, such that the first label is distinguishable from the second label, and the probes hybridize adjacently to each other at a nucleotide that distinguishes a $Pen^a$ allele from a $Pen^b$ allele; thereafter
 (ii) reacting said construct with a ligase in a reaction medium; and then
 (iii) analyzing said reaction medium to detect the presence of a ligation product comprising said first probe and said second probe.

18. A method as claimed in claim 17, wherein said Pen allele comprises a sequence that is encoded by at least nucleotide 526 of GPIIIa mRNA and said labeled oligonucleotide probe hybridizes to a nucleotide sequence which comprises or is adjacent to nucleotide 526 of GPIIIa mRNA.

19. A method for typing glycoprotein GPIIIa, wherein said method comprises the steps of:
 (a) obtaining a DNA molecule comprising a portion of the GPIIIa gene, wherein said portion includes nucleotide 526 of GPIIIa cDNA, and
 (b) analyzing said DNA molecule to determine Pen alloantigen phenotype.

20. The method of claim 19, wherein said DNA molecule is obtained by (a) isolating genomic DNA of a human individual, or (b) synthesizing cDNA from human mRNA.

21. The method of claim 20, further comprising the step of amplifying said genomic DNA or said cDNA to obtain said DNA molecule.

22. The method of claim 21, wherein said amplification step comprises performing a polymerase chain reaction.

23. The method of claim 22, wherein said amplification step is effected by using antisense and sense primers having the nucleotide sequences of SEQ ID NO:1 and SEQ ID NO:2, respectively.

24. The method of claim 19, wherein said analysis of said DNA molecule is performed by a technique selected from the group consisting of allele-specific oligonucleotide probing, ligase-mediated gene detection and fluorescence resonance energy transfer.

25. A kit for typing platelet Pen alloantigens, comprising an oligonucleotide for amplifying DNA that comprises at least a portion of a GPIIIa gene or GPIIIa cDNA, wherein said portion includes a nucleotide corresponding to nucleotide 526 of said GPIIIa cDNA.

26. The kit of claim 25, further comprising a receptacle containing a solution of a labeled oligonucleotide that distinguishes an allele of a platelet Pen alloantigen from another Pen allele.

27. A kit for typing platelet Pen alloantigens, comprising a receptacle containing a solution of an antibody that discriminantly binds either the alloantigen expressed by the Pen$^a$ allele of GPIIIA or the alloantigen expressed by the Pen$^b$ allele of GPIIIa, wherein said antibody is not obtained derived from human alloantisera.

* * * * *